(12) United States Patent
Moser et al.

(10) Patent No.: US 10,550,839 B2
(45) Date of Patent: Feb. 4, 2020

(54) PUMP MODULE AND DEVICE FOR PRODUCING A FLUID JET

(71) Applicant: Medaxis AG, Baar (CH)

(72) Inventors: Beat Moser, Uerzlikon (CH); Adrian Zweifel, Jona (CH); Beat Widmer, Lucerne (CH); Martin Butler, Hohenrain (CH); Lukas Christen, Lucerne (CH); Roman Good, Zürich (CH); Daniel Napoletano, Eglisau (CH)

(73) Assignee: Medaxis AG, Baar (CH)

( * ) Notice: Subject to any disclaimer, the term of this patent is extended or adjusted under 35 U.S.C. 154(b) by 332 days.

(21) Appl. No.: 15/622,469

(22) Filed: Jun. 14, 2017

(65) Prior Publication Data

US 2017/0356443 A1    Dec. 14, 2017

(30) Foreign Application Priority Data

Jun. 14, 2016    (EP) .................................... 16174463

(51) Int. Cl.
*F04B 53/22*    (2006.01)
*A61B 90/98*    (2016.01)
(Continued)

(52) U.S. Cl.
CPC .......... *F04B 53/22* (2013.01); *A61B 17/3203* (2013.01); *A61B 90/98* (2016.02);
(Continued)

(58) Field of Classification Search
CPC .... F04B 39/125; F04B 53/007; F04B 53/109; F04B 53/166; A61M 3/0258
See application file for complete search history.

(56) References Cited

U.S. PATENT DOCUMENTS 4,348,160 A * 9/1982 Heyneman ............ B01L 3/0206
                                                    222/334
5,451,145 A    9/1995 Sauter
(Continued)

FOREIGN PATENT DOCUMENTS

CN        1576579 A      2/2005
CN      201209546 Y      3/2009
(Continued)

OTHER PUBLICATIONS

Chinese Office Action , CN201710443843.2, dated Sep. 11, 2018.
European Search Report, EP16174463, dated Sep. 5, 2016.

*Primary Examiner* — Patrick Hamo
(74) *Attorney, Agent, or Firm* — Fishman Stewart PLLC

(57) ABSTRACT

A pump module and a device for producing a fluid jet with a pump module are disclosed. In an embodiment the pump module may include a pump housing in which at least one pump piston is mounted in a reciprocatingly movable manner and is provided with at least one sealing element which during a pumping operation interacts with a cylinder. For creating such a pump module producible in a simple manner and nevertheless exhibiting the functionality necessary for the pumping operation, embodiments disclose a valve block, which receives at least one valve associated with the cylinder, wherein the cylinder is sealed against the valve block. Furthermore, a cover element may abut against the valve block on a side opposite to the cylinder and between itself and the valve block forms an inlet passage leading to the cylinder and/or an outlet passage communicating with the cylinder.

14 Claims, 15 Drawing Sheets

(51) Int. Cl.
*A61B 17/3203* (2006.01)
*F04B 19/22* (2006.01)
*F04B 53/10* (2006.01)
*F04B 53/16* (2006.01)
*A61B 90/00* (2016.01)

(52) U.S. Cl.
CPC .............. *F04B 19/22* (2013.01); *F04B 53/10* (2013.01); *F04B 53/16* (2013.01); *A61B 2090/034* (2016.02)

(56) References Cited

U.S. PATENT DOCUMENTS

| | | | | |
|---|---|---|---|---|
| 6,095,758 | A * | 8/2000 | Chou | F04B 35/04 417/374 |
| 7,828,972 | B2 * | 11/2010 | Ham | B01D 61/06 210/321.66 |
| 8,246,330 | B2 * | 8/2012 | Ay | F04B 39/12 417/313 |
| 8,251,679 | B2 * | 8/2012 | Kuehner | A61B 17/3203 417/413.1 |
| 10,240,596 | B2 * | 3/2019 | Wandel | F04B 1/02 |
| 2005/0008506 | A1 | 1/2005 | Lanfredi | |
| 2008/0246222 | A1 | 10/2008 | Adler et al. | |
| 2009/0242470 | A1 * | 10/2009 | Muenkel | B01D 35/30 210/148 |
| 2012/0051956 | A1 * | 3/2012 | Grip | F04B 53/22 417/413.1 |
| 2014/0079580 | A1 | 3/2014 | Habe | |

FOREIGN PATENT DOCUMENTS

| | | |
|---|---|---|
| DE | 29611935 U1 | 9/1996 |
| DE | 10160168 A1 | 6/2003 |
| DE | 102006053609 A1 | 5/2008 |
| EP | 0398209 A1 | 11/1990 |
| JP | S56-057975 U | 5/1981 |
| JP | H09177973 A | 7/1997 |
| JP | 200404769 A | 1/2004 |
| JP | 2009503346 A | 1/2009 |
| JP | 2009287570 A | 12/2009 |
| JP | 2014061376 A | 4/2014 |
| WO | WO-2008086950 A1 | 7/2008 |
| WO | 2014095781 A1 | 6/2014 |

* cited by examiner

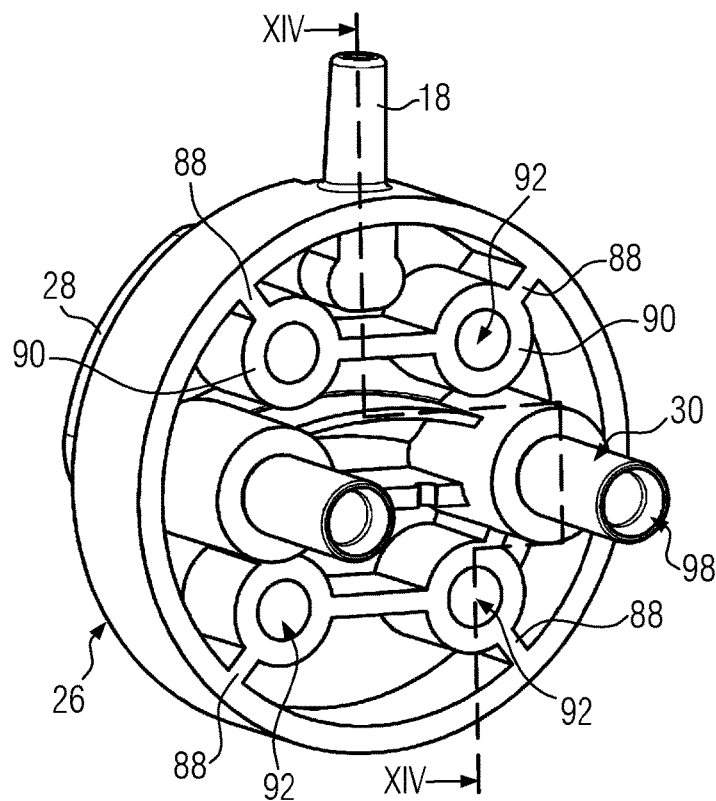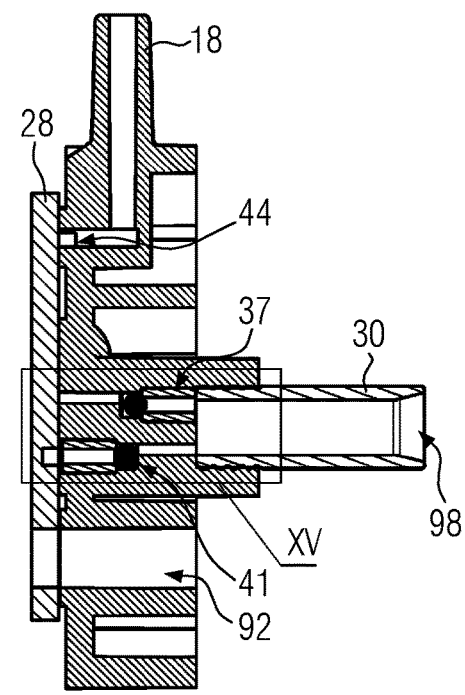
FIG. 13   FIG. 14
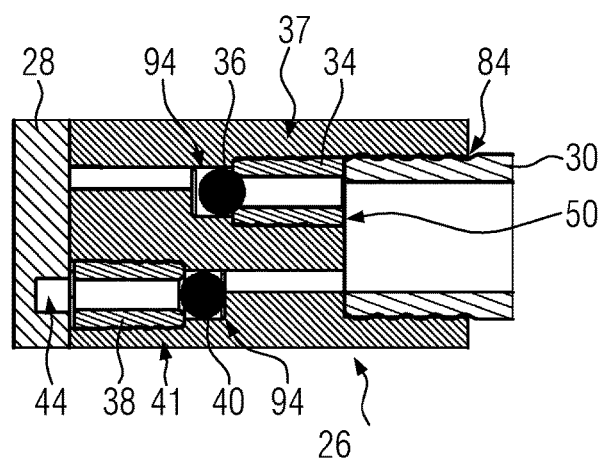
FIG. 15

PUMP MODULE AND DEVICE FOR PRODUCING A FLUID JET

CROSS-REFERENCE TO RELATED APPLICATIONS

This application claims priority to European Patent Application No. 16174463.6, filed Jun. 14, 2016, the contents of which are hereby incorporated by reference in its entirety.

TECHNICAL FIELD

The present invention relates to a pump module and a device for producing a fluid jet. The pump module according to the invention is used as part of the device for producing the fluid jet.

BACKGROUND

The present invention is intended to in particular specify a pump module which is applied for as a consumable part. The pump module according to the invention is intended to be particularly suitable for debridement by way of a water jet. In this treatment, a water jet is directed at a wound to clean the wound and, for example, remove scab. Wound healing has always been enhanced by debridement.

A pump module with a pump casing in which at least one pump piston is mounted in a reciprocatingly movable manner which is provided with at least one sealing element that is sealingly received in the pump casing during the pumping operation, is known, for example, from US 2014/0079580 A1. Further pump modules for debridement by way of a fluid jet are known from prior art, for example, from US 2011/0150680 A1, US 2002/0176788 A1 or US 2010/0049228 A1. These prior art documents already show the efforts of the expert community to provide a pump module which is detachably connected to a drive in order to provide a device for producing a fluid jet in which the module is the consumable part. The pump module therefore has a relatively simple and inexpensive structure.

SUMMARY

The present invention is also based on the problem of proposing a pump module of the type mentioned at the outset which can be produced in a simple manner but nevertheless has the functionality required for the pumping operation.

In view of this, the present invention proposes a pump module with a valve block which receives at least one valve to the cylinder and is sealed against the cylinder. However, the valve is usually provided in the form of a valve liner in the valve block. Preferably, the valve block comprises the inlet and the outlet valve to each cylinder, preferably in the form of valve liners with associated valve bodies for the inlet and outlet valves. In addition, the valve block usually forms inlet passages leading to the inlet valve and outlet passages leading away from the outlet valve. These passages are preferably on the side of the valve block facing away from the cylinder provided as manifolds for several valves and/or on the surface of the valve block, commonly on a substantially planar surface which forms the valve block on the side opposite the cylinder. This side facing away from the cylinder is covered by a cover element which abuts against the valve element and forms the inlet passage or the outlet, respectively, between itself and the valve block. The inlet or outlet passage is commonly shaped as a recessed groove which is exposed toward the surface of the cover element and/or the valve block and which by the interaction of the valve block and cover element becomes a circumferentially closed passage which passes the fluid to be delivered with the pump toward the cylinder or discharges it from the cylinder.

This embodiment makes it possible to produce the essential element of a pump with inlet and/or outlet valves in a simple manner. The valve block is there commonly provided with recesses which extend either at a right angle to the direction of motion of the reciprocatingly movable pump piston or parallel thereto. In view of a simple fabrication of the valve block, the latter is usually formed to be disk-shaped. The bores accommodating a valve and also the inlet and outlet passages are there commonly recessed extending parallel to the direction of motion of the pump piston. These recesses are there preferably produced by way of injection-molding so that the valve block exhibits the necessary seats for the valves and the flow passages without any finishing work. Preferably, a single passage can extend at a right angle thereto and form a connecting line for supplying fluid to the pump module. For this purpose, it can be necessary to provide the injection mold with a movable core. Beyond that, however, the injection mold can be designed in a very simply manner for forming the necessary flow guides into the valve block for the fluid toward the cylinder and away from the cylinder.

Similarly, the cover element is preferably shaped as a disk. Here as well, grooves can be recessed on one or both main side surfaces of the disk and form the flow passages. The cover element is commonly also produced as an injection-molded member in the final contour, i.e. no further finishing work is required. All the recesses provided in the cover element, which can be designed in the form of a groove or a through bore, extend preferably parallel to the direction of motion of the pump piston.

It arises with these explanations that the combination of the valve block and the cover element indicates a central element of the pump module which can be produced in a simple manner by injection-molding and forms the flow passages leading to the cylinder or cylinders and accommodates the valve or valves therein. The valves can there be designed in the form of valve liners which form a movable valve body and a valve opening which in the closed state of the valves cooperates with the valve body. The valve liners can be made of plastic material or metal and can be pressed into the valve block. The valve block itself there commonly forms a receiving space which in the direction of flow is upstream of the valve opening and accommodates the movable valve body so that the latter can move from its open to its closed position, preferably solely due to the pressure difference acting on the valve body. The valve body is there preferably formed by a freely movable valve ball which can commonly completely close the valve opening.

The valve block can integrally form the cylinder or the cylinders. In one such embodiment, the integrally formed component is preferably produced by way of plastic injection molding and made from plastic material. The valve block preferably does not form the cylinder itself. Instead, this cylinder is commonly mounted as a separate component and sealingly connected to the valve block. Accordingly, a cylinder insert is proposed according to a preferred development of the present invention and forms the cylinder and abuts sealingly against the valve block. This cylinder insert can be formed from plastic material, in particular high-quality plastic material, or metal. The cylinder insert there has a surface quality to be expected from cylinders in the region of the inner circumferential surface which interacts in a sealing manner with the sealing element of the pump piston. The cylinder insert can be accommodated in a casing base and can be pressed against the valve block via this casing base, in particular pressed against it in a sealing manner. Alternatively, the cylinder insert can also be press-fitted to the valve block such that a tight connection is established between the valve insert and the valve block. It is equally conceivable to insert-mold the cylinder insert when producing the valve block in the injection-molding process in order to create an intimate connection between the valve insert and the valve block. The cylinder insert can also be glued or welded to the valve block. A fluid-tight connection between the valve block and the cylinder insert must there be ensured.

For press-fitting the cylinder insert to the valve block, the latter commonly comprises a ring-shaped projection which extends over a certain length of the cylinder insert and surrounds it circumferentially and in a sealing manner. For the best possible press-fit of the cylinder insert, the latter commonly as an outer circumferential surface comprises a contouring or corrugation which together with an inner circumferential surface being formed by the valve block interacts in a sealing manner and holds the cylinder insert in a positive-fit manner.

The cover element is there preferably connected directly to the valve block. This connection is preferably such that the cover element in a sealing manner seals the recesses provided in the phase boundary between the cover element and the valve block, thereby forming the inlet and outlet passages. The direct connection is there preferably formed by welding. Accordingly, the cover element is preferably formed from preferably transparent plastic material which is permeable to a laser, whereas the valve block is formed from plastic material which is impermeable to laser beams. The cover element can therefore from the side opposite the cylinder be welded to the valve block by way of laser beam welding. Laser beams are there guided through the cover material to the phase boundary and there converted to heat. With regard to uniform welding, it has proven to be advantageous to form the cover element substantially as a flat disk. The cover element accordingly comprises preferably two coplanar main side faces, of which one side surface in a sealing manner abuts directly against the valve block, and the other side is formed preferably in a flat manner to be adapted for introducing laser beams for welding. Other conceivable joining methods for producing the connection are ultrasonic welding, mirror welding, cold welding or gluing.

In view of the simplest possible production and assembly of the pump module, a preassembled pump unit is according to a preferred development of the present invention proposed which comprises at least one cylinder insert, the valve block, and the cover element. The components of this pump unit are fixedly connected to each other so that the pump unit can be handled as a single component during the assembly of the pump module. This pump unit commonly also comprises the valve bodies for the inlet and outlet valves which are preferably disposed upstream of valve liners or received in such valve liners. The outlet for the fluid conveyed in the pump unit is commonly formed by a bore recessed in the cover element. The corresponding outlet is preferably recessed in the main side surface of the cover element disposed opposite from the cylinder. This outlet can be in communication with a stud-shaped outlet port which is directly connected to the cover element, for example, fastened thereto or formed integrally thereon. However, the outlet port is preferably provided on a head element which is arranged upstream of the cover element and there abuts tightly against the cover element, so that the outlet port provided on the head element is commonly in communication with the outlet of the cover element and is provided in axial extension thereto, i.e. in the continuation of the direction of motion of the pump piston. Accordingly, the preferably stud-shaped outlet port is preferably located on one face side of the pump module. The outlet port can be provided with a thread for fastening a Luer connection for connecting a pressure hose to the pump module.

This head element is preferably by way of at least one tensioning element in abutment in a sealing manner commonly with the interposition of a sealing element, for example a sealing ring, where the tensioning element passes through the cover element and the valve block. The tensioning element also passes through a casing base possibly provided. If a head element is omitted, then the tensioning element is otherwise in abutment. The tensioning element is preferably a tensioning screw which commonly extends in the direction of motion of the pump piston. The thread-side end of the tensioning element is connected either to the head element, or to the cover element, or to a nut which is arranged upstream of the head element or the cover element, respectively. The tensioning screw can be in threaded engagement with the head element and/or the cover element.

The above-mentioned casing base is preferably provided to form guide and locking surfaces for detachably fastening the pump module to a drive casing of a drive, the drive pusher of which is connectable to the pump piston for reciprocating operation of the pump piston. The preferably provided casing base thus assumes the function of adapting the pump unit to the drive. The casing base can also have the function of holding all functional elements of the actual pump unit and accommodating or surrounding them in an aesthetically pleasing form. The pump unit preferably comprises a front discharge region which can seat the valve block and/or the head element. This seat is preferably designed on a substantially cylindrically shaped casing base as a recess open on the face side. Furthermore, the casing base preferably comprises a rear drive region which seats the cylinder and/or the pump piston. The cylinder or the pump piston, respectively, can there completely or partially in the axial direction be covered by the casing base.

The casing base can further comprise a guide sleeve associated with the pump piston. This guide sleeve is commonly located upstream of the actual cylinder and serves to guide the pump piston during the pumping operation. The guide sleeve is commonly not that region in which the piston with its sealing element is received in a sealing manner during the pumping operation and in which the fluid to be delivered is compressed. The respective guide sleeve instead preferably serves solely to guide the pump piston approximately in the middle length range thereof.

The pump module can comprise one or more pump pistons with associated cylinders. At least two pump pistons with associated cylinders are preferably provided, which are each provided to be eccentric relative to a longitudinal axis of the elongate pump module, so that the pump module is fastened to the drive casing by axial displacement and rotation in the manner of a bayonet closure where a positive-fitting connector between the pump pistons and the drive pushers of the drive can at the same time be formed. In view of this, each pump piston preferably comprises a positive-fit element which is connectable to a positive-fit counter-element of the drive pusher to transmit a reciprocating cyclic axial motion of the drive pusher to the pump piston in a manner substantially free of play.

According to a further preferred embodiment of the present invention, it is proposed that the inlet passage is in communication with at least two cylinders and the inlet passage is formed within the phase boundary between the cover element and the valve block such that the inlet passage at least partially circumferentially surrounds the outlet passage. The outlet passage is then located within the inlet passage, where passage sections leading to the inlet valve accommodate the outlet passage between themselves and an inlet port which is commonly provided at the upper side of the valve block. With proper alignment of the pump module, this configuration leads to the respective inlet being lower than the outlet, whereby the introduction of air bubbles into the rear side of the pump module is with certainty prevented.

According to a further preferred embodiment of the present invention, a transponder element is attached to the casing. This transponder element carries information about the maximum service life of the pump module, i.e., information that is suitable to indicate the operating time over which the pump module can be employed. The transponder element can also forward information on the efficiency to a drive device into which the pump module according to the invention is inserted. The drive device there communicates indirectly or directly, for example, by way of a handpiece, which is marketed as consumable material together with a nozzle geometry adapted to the particular application, in order to transmit information to the drive device about the expected operating point of the nozzle cross-section. This embodiment makes it possible to adapt the operating point of the drive device to the efficiency of the pump module together with the handpiece and the nozzle cross-section provided therein. The transponder can there comprise a coil with which the signal from the handpiece is received, amplified and forwarded in the direction of the drive device. The transponder element also contains information for positioning the pump module relative to the drive casing. This ensures that the drive is due to the positional information of the pump module only started when proper fastening of the pump module to the drive casing has been established. The respective information of the transponder element is commonly read out by a reading unit which is provided on the drive casing. The reading unit can there preferably be provided in the circumferential direction of a substantially cylindrical pump module at a predetermined location and receive and thereby read out the positional information only when the pump module has been set to the correct position by way of a bayonet motion. The transponder element can also only inform the drive device that a pump module is provided as a consumable part in the region of the drive device, whereas the correct installation position of the pump module relative to the drive device can be indicated by a switch which is actuated only when the pump module has been fixed in the correct orientation on the drive casing. Both measures can there be coupled to one another in order to be able to operate the drive device, even in the event of a possibly bridged switch, only when a pump module with a transponder element is in fact provided in the vicinity of the drive device.

BRIEF DESCRIPTION OF THE DRAWINGS

Further details and advantages shall arise from the following description of an embodiment in combination with the drawing, in which:

FIG. 13 shows a perspective rear view of the pump unit according to FIG. 2;

FIG. 14 shows a sectional view along line XIV-XIV, according to the view in FIG. 13;

FIG. 15 shows detail XV according to FIG. 14;

DETAILED DESCRIPTION

Figure 1:
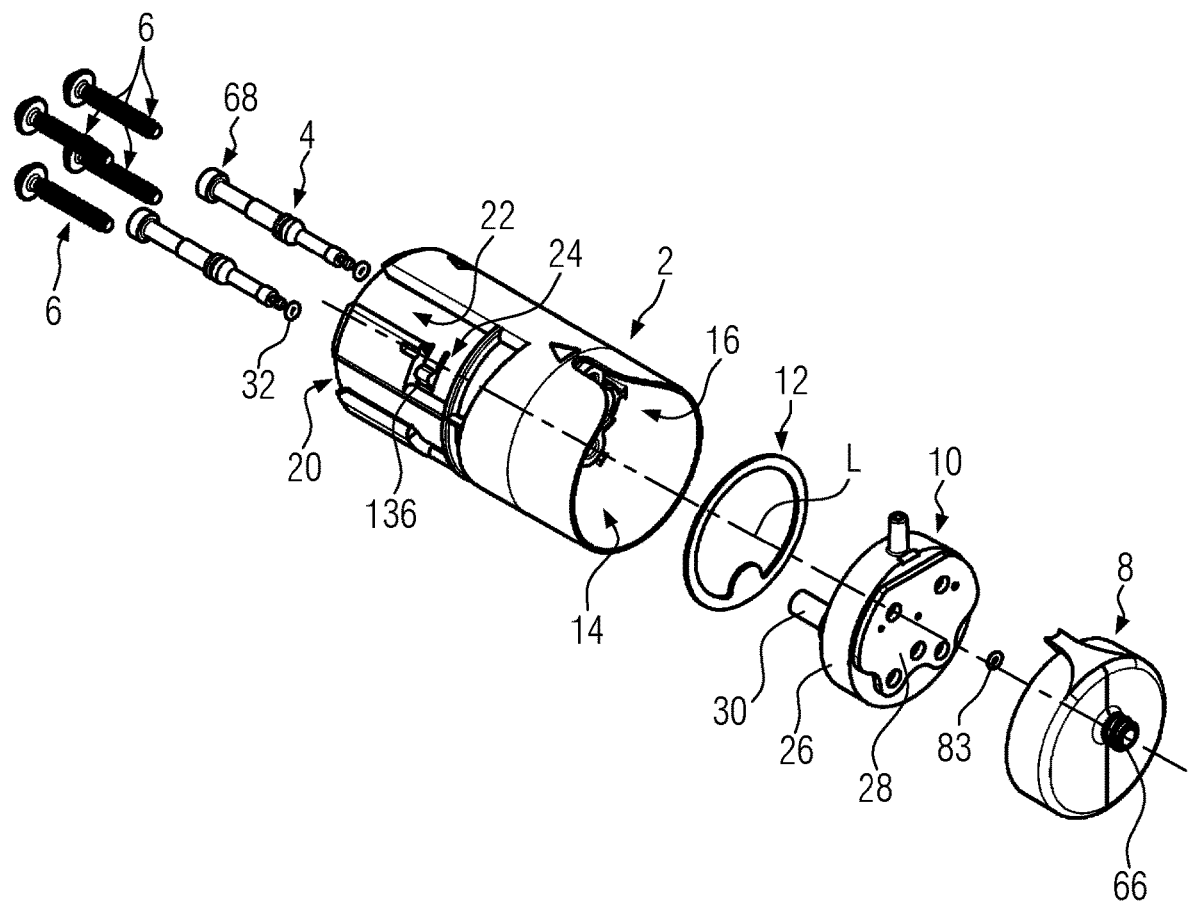
FIG. 1 shows a first exploded view of the embodiment.

FIG. 1 shows the essential components of the embodiment according to the present invention, which is a pump module. The pump module comprises a casing base 2 which accommodates two plunger bodies 4 within itself and surrounds them in a reciprocatingly movable manner. Furthermore, four tensioning screws 6 are shown which are embodiments of tensioning elements within the meaning of the present invention and in the assembled state engage with a head element 8 that is disposed before a pump unit 10 being received in casing base 2 while an annular RFID element 12 is interposed, which is an example of a transponder unit of the present invention. The casing base 2 for this purpose has a discharge region 14 which is configured as a cylindrical seat on the casing base 2, where an axial slot 16 is formed adapted to receive an inlet port 18 of the pump unit 10. The casing base 2 is likewise open at the end opposite to the discharge region 14 and forms a drive region 20.

Figure 18:
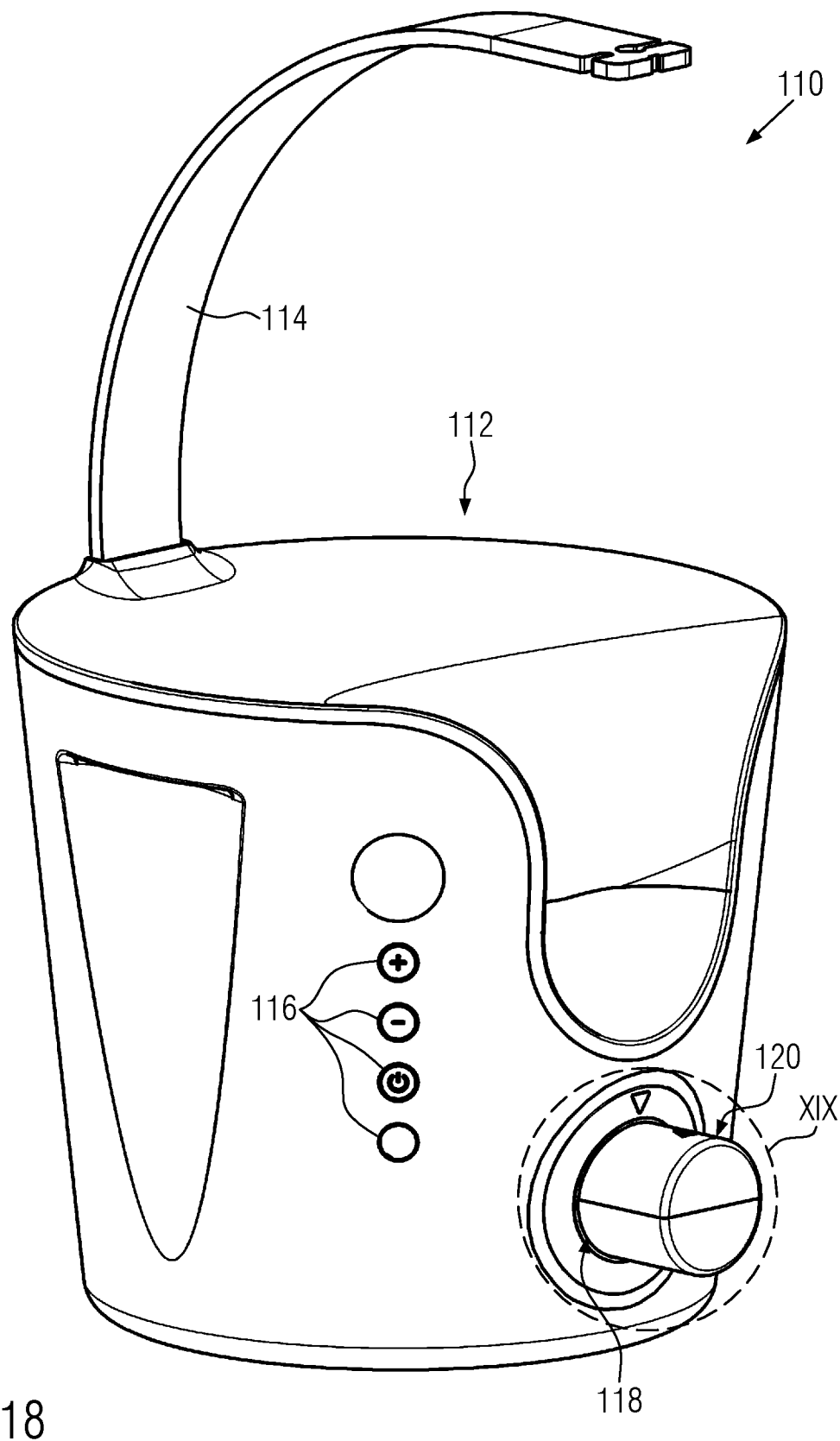
FIG. 18 shows a perspective view of an embodiment of a device for producing a fluid jet.

As can be seen in FIG. 1, the casing base is formed to be substantially cylindrical. Formed on the outer circumferential surface on the casing base 2 are grooves 22 extending in the axial direction of the casing base 2 and transverse grooves 24 branching therefrom and extending transversely thereto which represent the guide and locking surfaces for attaching the pump module to a drive casing, the details of which are illustrated in FIG. 18 et seqq. and the associated description.

The pump unit 10 is formed by a valve block 26 and a cover element 28 abutting thereagainst, where two cylinder inserts 30 project from the valve block 26 on the side disposed opposite to the cover element 28, of which only one cylinder insert 30 can be seen in FIG. 1 and which during the pumping operation interact with the plunger bodies 4. For this purpose, the plunger bodies 4 each carry a sealing element 32 in the form of a sealing ring which is in the region of the front free end of the plunger body 4 held thereon in a positive-fit manner.

Figure 2:
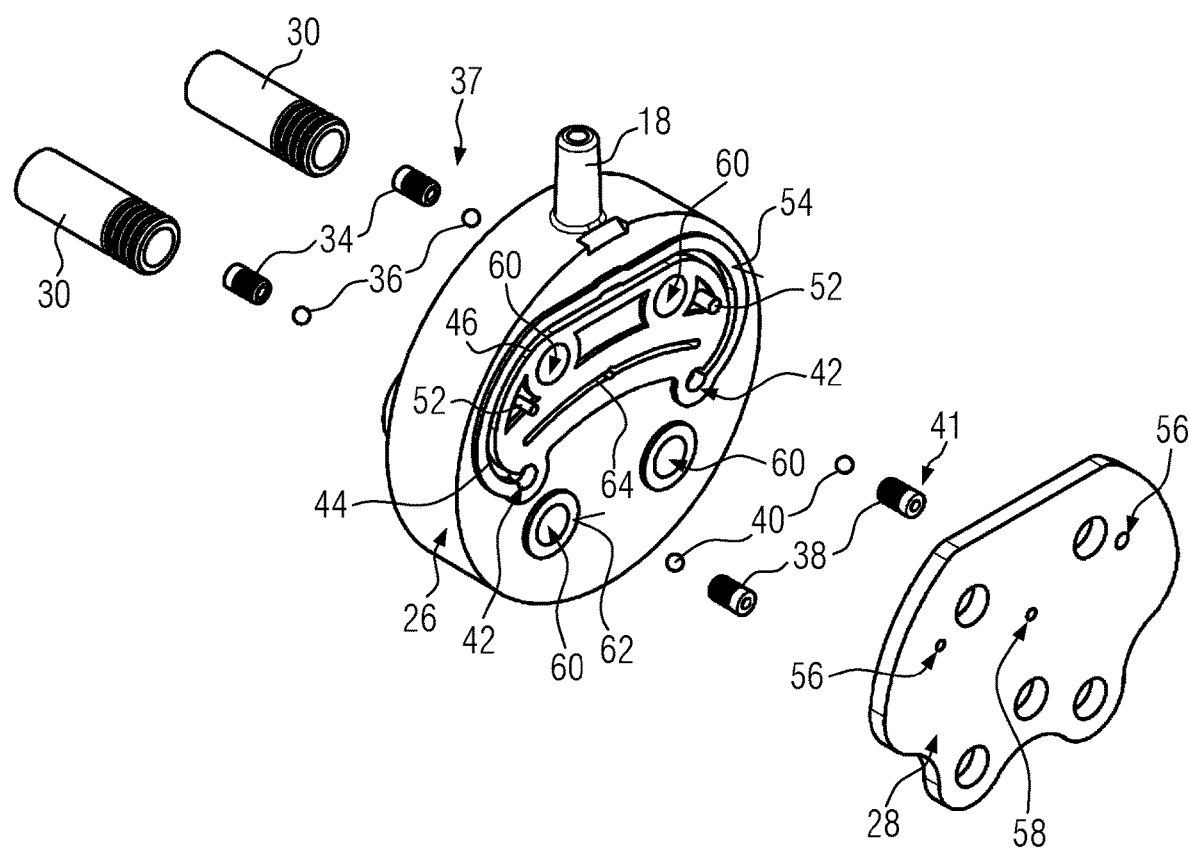
FIG. 2 shows an exploded view according to FIG. 1 for a pump unit of the embodiment shown in FIG. 1.

FIG. 2 shows that the two cylinder inserts 30 on their end facing the valve block 26 comprise a wavelike contour on their outer circumference which are formed into the valve block 26 for the sealing insertion of the cylinder inserts 30. A respective valve liner 34 is provided between the cylinder inserts 30 and the valve block 26 and together with a valve ball 36 each forms an outlet valve 37. Valve liners 38 with associated valve balls 40 are illustrated on the side opposite to the cylinder inserts 30 and form inlet valves 41 to the respective cylinder inserts 30. The inlet valves 41 are received in inlet valve bores 42 which are recessed in the valve block 26 and communicate with an inlet passage 44 which is recessed in a projection 46 as a U-shaped groove being open on one side and which is covered by the cover element 28. The outlet valves 37 are seated in corresponding outlet valve bores, one of which is shown by way of example in FIG. 9 and is provided with reference numeral 50. As illustrated in FIG. 2, inlet port 18 is integrally formed on the valve block 26. From the side facing the cover element 28, two fitting elements 52 of different diameters protrude from and project beyond the sealing surface 54 formed by the projection 46. The cover element 28 has bores 56 formed adapted for these fitting elements 52 which serve to correctly position the cover element 28 relative to the valve block 26. The fitting elements 52 and the fitting bores 56 there have mutually adapted diameters so that the cover element 28 is according to a poka-yoke function always arranged in the correct orientation and position when assembling the cylinder insert 30 on the valve block 26.

In addition to these two fitting bores 56, the cover element 28 also comprises an outlet bore 58.

The valve block 26 comprises four through bores 60 corresponding to the tensioning screws 6 and which, firstly, pass through the sealing surface 54 formed by the projection 46 and, secondly, annular surfaces 62 which are configured to be adapted for the abutment against the cover element 28 and are provided at the same height. The cover element 28 abuts sealingly against the surfaces 62 and 54 and is welded thereon by laser beam welding. For this purpose, the cover element 28 is formed from laser-transparent material, whereas the valve block 46 is formed from plastic material absorbing laser beams. Both parts can accordingly be connected by way of laser transmission welding, where the cover element 28 made of plastic material is at the phase boundary to the valve block connected in a positive substance-fit manner to the plastic material of the valve block 26. The inlet passages 44 and an the outlet passages, designated by reference numeral 64 and comprising a U-shaped channel recessed on the valve block 26 and covering the cover element 28, are formed thereby. The outlet passage 64 is via the outlet bore 58 in communication with an outlet port bushing 66 being integrally formed on the head element 8 and being provided in axial extension of the outlet bore 58 and provided with an external thread on its outer circumference for forming a Luer connection. A pressure hose can accordingly by way of a Luer connection be connected in a simple way to the outlet port bushing 66.

Figure 4:
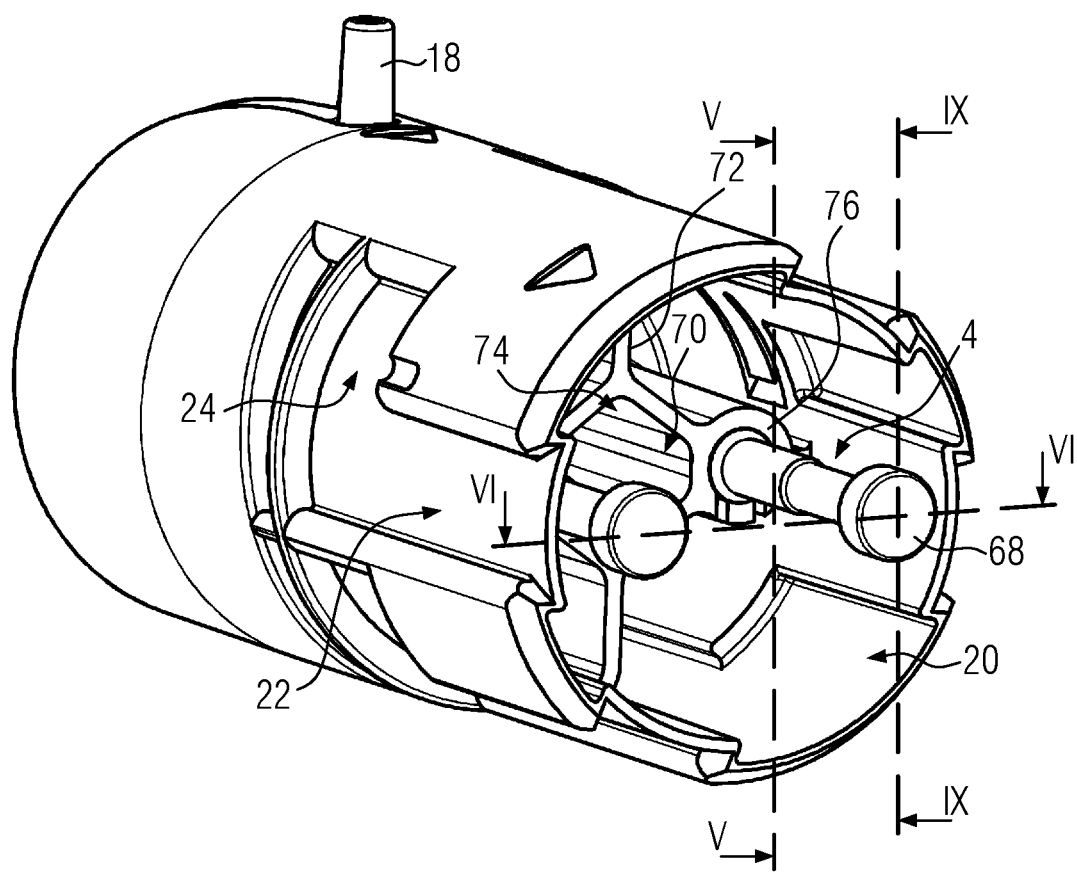
FIG. 4 shows a perspective side view according to FIG. 3 into the open drive region.

FIG. 4 shows a perspective side view with a top view upon the face side end of the casing base 2 and of the drive region 20. The plunger bodies 4 are surrounded by the casing base 2 and with their one end project into the drive region 20. As is in particular evidenced by FIG. 5, the end of the plunger body 4 on the drive side, which forms a positive-fit element shaped as a hammer head 68, projects beyond the casing base 2 at the end side. Otherwise, however, the plunger body 4 is axially covered by the casing base (see FIG. 5).

As can be seen from a synopsis of FIGS. 4, 5, 6 and 11, the casing base 2 is configured as an injection-molded member with relatively uniform wall thicknesses, so that good solidification behavior is obtained during the injection-molding process of the casing base 2. Plastic materials for the production of the components of the module can be PA, PE, PP and/or POM, possibly as filled plastics, for example, filled with minerals and/or fibers. For this purpose, the casing base 2 has a center recess 70 which is via radial webs 72 connected to the outer circumferential surface of the casing base 2, where the radial webs 72 branch off from a polygon structure 74 which connects guide sleeves 76 between the radial webs 72 inwardly to the respective plunger bodies 4 which are supported via further radial webs 78 on the outer circumferential surface of the casing base 2 (cf. FIG. 16).

Figure 17:
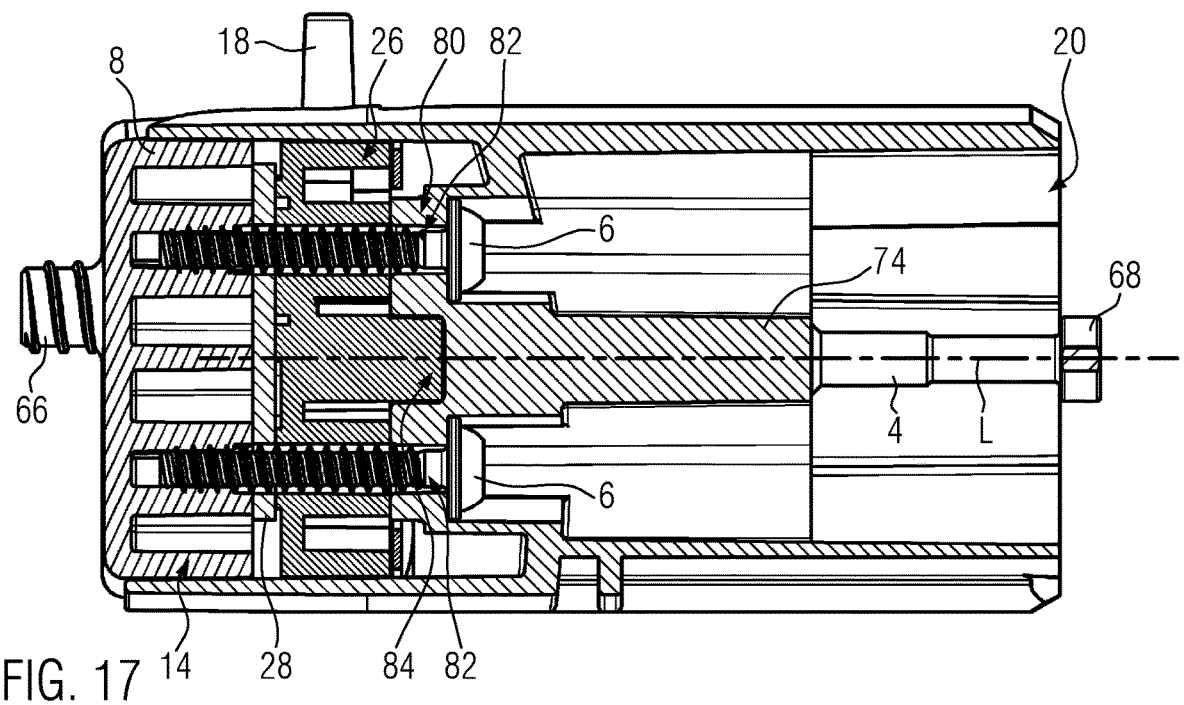
FIG. 17 shows a sectional view taken along line XVII-XVII according to FIG. 16, where the sectional plane includes the center longitudinal axes of the two tensioning screws 6 and extends parallel to the plane of motion of the pump piston.

The casing base 2 forms a radially extending partition wall 80 which is inter alia provided with passage bores 82 for the tensioning screws 6 (cf. FIG. 17). The tensioning screws 6 there completely penetrate the partition wall 80, the valve block 26 and the cover element 28, and partially the head element 8 and are in threaded engagement with the latter. For this purpose, the tensioning screws 6 are self-tapping. The head element 8 can also by welding be welded to the recess formed by the casing base 2 in the discharge region 14 and thereby be indirectly connected to the valve block 26 and the cover element 28. A sealing ring 83 seals the passage formed by the outlet port bushing 66 against the outlet bore 58 of the cover element 28 (cf. FIGS. 1 and 5).

Figure 8:
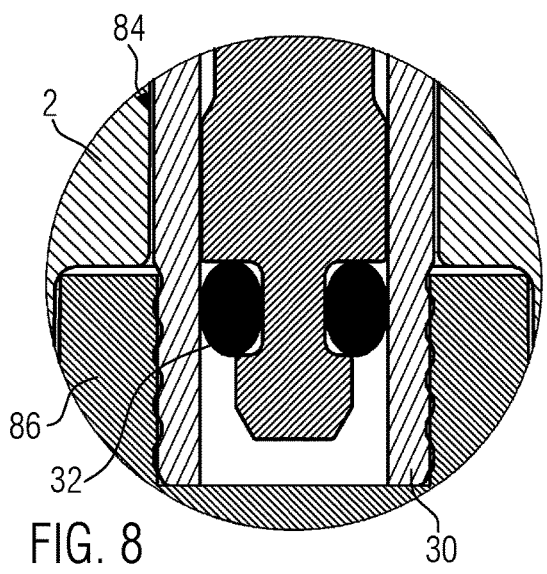
FIG. 8 shows enlarged detail VIII according to FIG. 6 for a pump piston penetrating deeper into the cylinder than in FIG. 6.

In the axial extension of the guide sleeves 76, the casing base 2 forms cylinder insert receiving bores 84 reaching up to the partition wall 80 which are formed adapted to receive the cylinder inserts 30 and which are radially thickened approximately at the height of the partition wall 80 in order to form between the cylinder insert 30 and the material of the casing base 2 an annular space into which a protruding ring collar 86 of the valve block 26 fits. This ring collar 86 is shown, for example, in FIGS. 6 and 9. The ring collar 86 serves to establish the sealing connection between the cylinder insert 30 and the valve block 26. As illustrated in FIG. 8, a contoured outer circumferential surface of the cylinder inserts 30 is there accommodated within the ring collar 86 and is also positively locked therewith Each cylinder insert 30 is by pressing inserted into the ring collar 86 and is thereby sealingly connected to the valve block 26.

Figure 5:
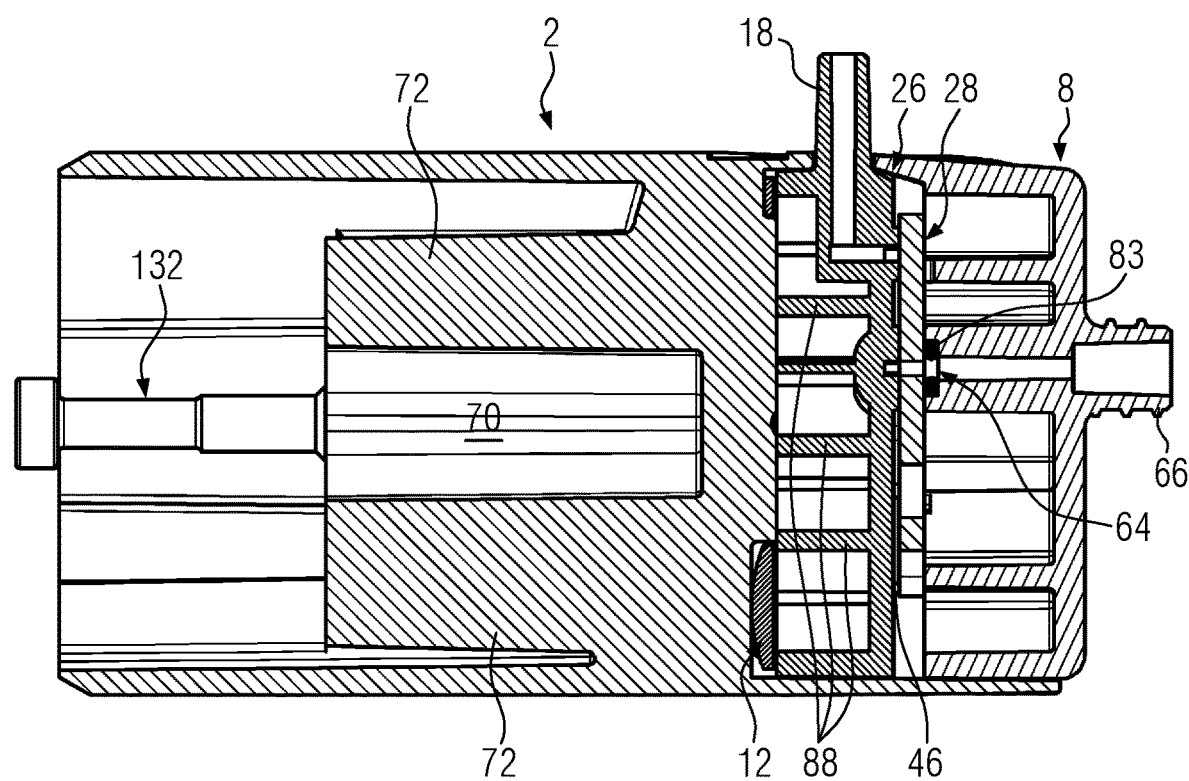
FIG. 5 shows a sectional view along the line V-V according to FIG. 4 and FIG. 11, respectively, where the sectional plane includes the center longitudinal axis of the pump module.

The partition wall 80 further forms an annular groove which opens toward the valve block 26 and is formed adapted to receive the RFID ring 12 so that this RFID ring 12 can be arranged between the partition wall 80 and the valve block 26 (cf. FIG. 5) FIG. 5 there in the lower part of this annular groove shows a thickening of the RFID ring 12 which represents the data carrier. The remainder of the region of the RFID ring 12 being slimmer in the radial direction serves for adequate positioning within the casing base 2 (cf. FIG. 1) and also as a coil for signal amplification of a signal output, for example, from a handpiece, with which the type of nozzle geometry installed in the handpiece is indicated.

As illustrated in FIGS. 5 and 13, the valve block 26 is also configured as a component having the same wall thicknesses and can therefore be produced well by way of plastic injection molding. in particular FIG. 5 illustrates several of support ribs 88 extending in the direction of motion of the plunger bodies 4 and being supported on the partition wall 80 and connecting sleeve segments 90 which form passage bores 92 for the tensioning screws 6 that are flush with the passage bores 82 through the partition wall 80, where the above-mentioned sleeve segments 90 form the previously mentioned annular surfaces 62 for abutment of the cover element 28.

FIGS. 14 and 15 illustrate the arrangements of the inlet and outlet valves 37, 41 in the valve block 26. This valve block 26 has bores 42, 50 being adapted to receive the corresponding valve lines 34 and 38, and each of which having a receiving space 94 downstream in the flow direction of the fluid in which the valve ball 36 or 40 are respectively located. In the closed state of the valve, this valve ball 36 or 40, respectively, interacts with a valve opening which is formed by the flow-free end of the corresponding valve liner 34, 38. This position is in FIG. 15 shown for the valve ball 36 of the outlet valve 37, whereas the valve ball 40 of the inlet valve 41 unblocks the corresponding valve opening. FIG. 15 shows a state in which the plunger body 4 increases the displacement within the cylinder insert 30 and the fluid to be pumped is introduced into the displacement chamber through the inlet passage 44, whereas the outlet passage is closed by the outlet valve 37. The respective valve balls 36, 40 are in the embodiment shown provided freely movably in the receiving space 94 and are captively held in the valve block 26 due to the diameter ratios between the valve opening and the diameter on the flow-remote side of the passage which branches from the valve opening and is formed in the valve block 26. For assembly, the respective ball 36, 40 is first inserted into the receiving space 94. The valve liner 34 or 38, respectively, is then pressed into the valve block 26. The valves 37, 41 are then preassembled in the valve block 26 in a captive manner.

As can further be seen in FIG. 15, the cylinder insert 30 pressed into the valve block 26 on the face side abuts against the valve liner 34 of the outlet valve 37, whereby the valve 37 provided on the pressure side of the pump is additionally secured in position and prevented from being undesirably pressed out from the force fit to the valve liner 36.

Figure 6:
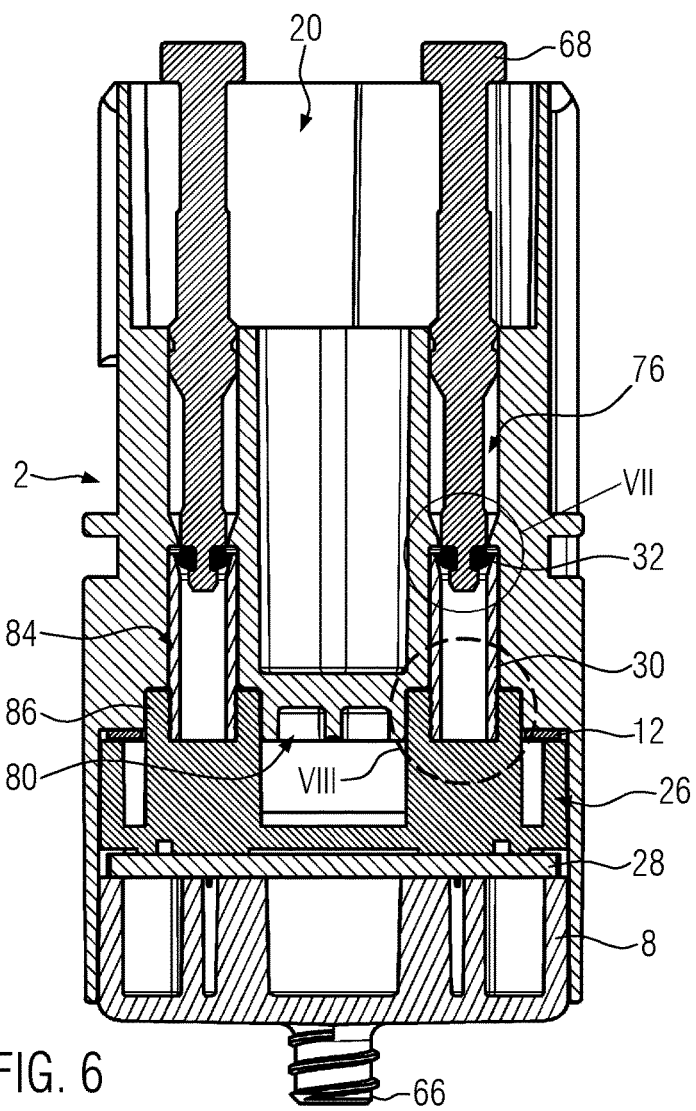
FIG. 6 shows a sectional view along the line V-V according to FIG. 4, where the sectional line includes the plane of motion of the pump piston.
Figure 7:
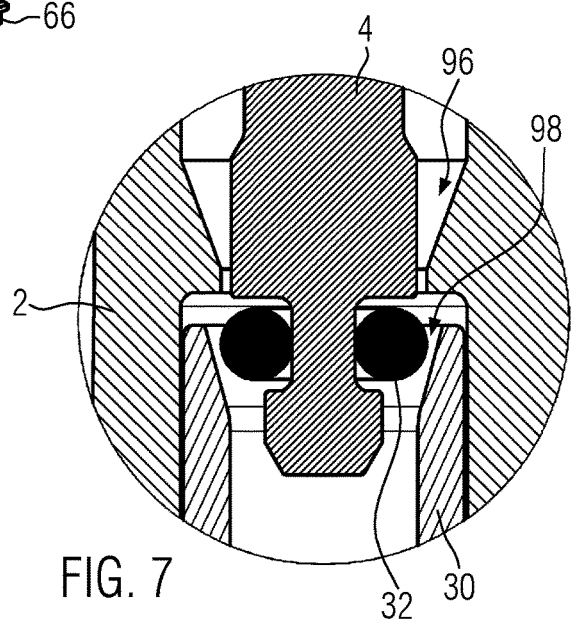
FIG. 7 shows enlarged detail VII according to FIG. 6.
Figure 9:
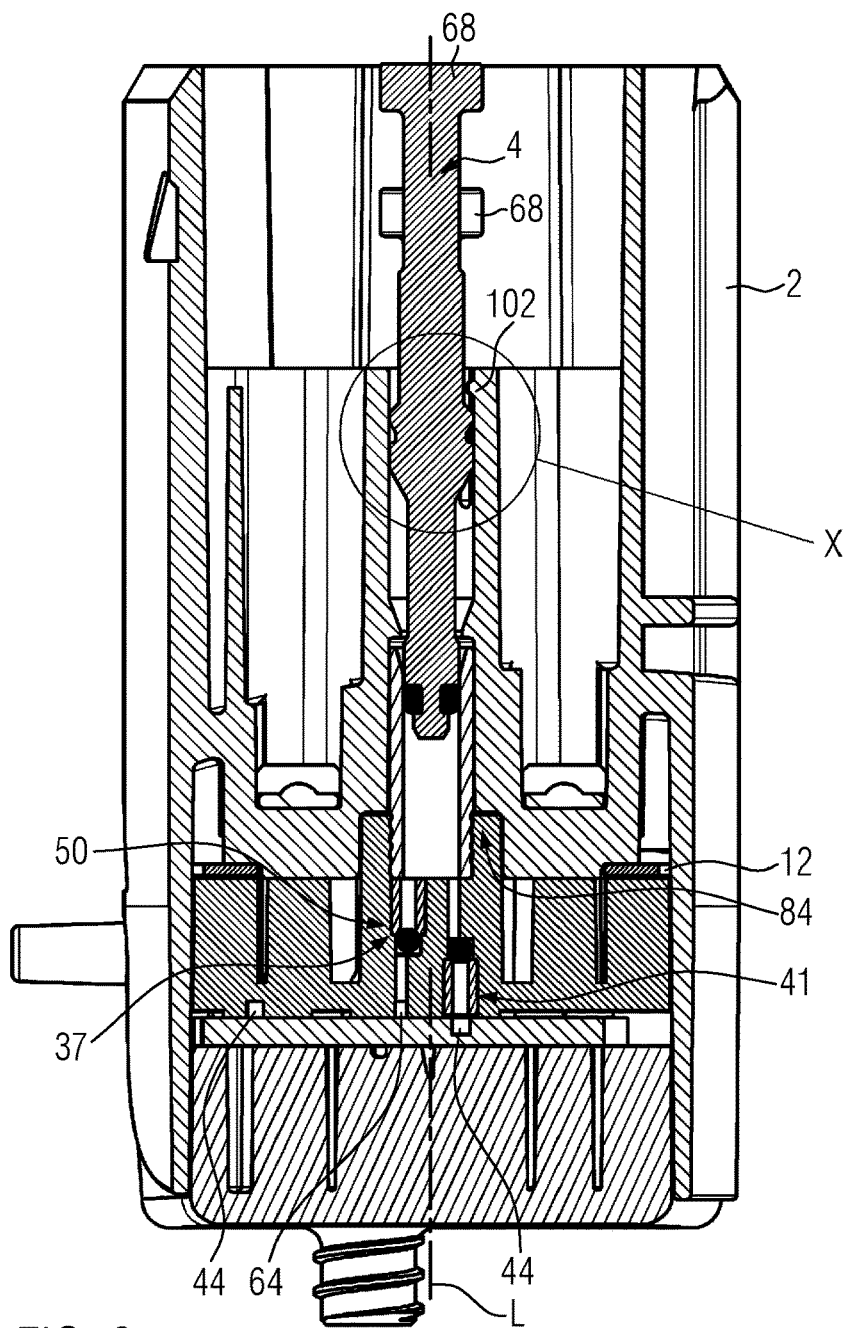
FIG. 9 shows a sectional view along line IX-IX according to FIG. 4, where the sectional plane includes the plane of motion and the center longitudinal axis of one of the pump pistons.
Figure 10:
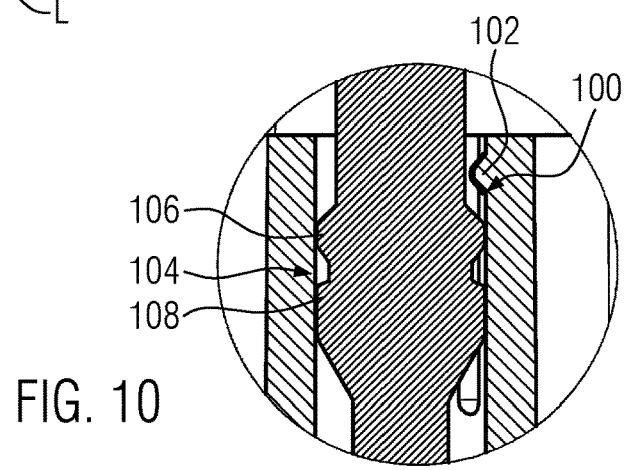
FIG. 10 shows enlarged detail X according to FIG. 9.

In particular FIG. 7 illustrates a first tapered feed-in device 96 which is formed by the casing base 2 and which is provided before the cylinder insert 30 in the direction of the drive region 20. This first tapered feed-in device 96 facilitates the insertion of the plunger body 4 with its front end, on which the sealing element 32 is located, into the cylinder formed by the cylinder insert 30. When the plunger body 4 is inserted, the sealing element 32 is arranged concentrically with respect to the cylinder insert 30 and brought approximately to the latter's inner diameter. A second tapered feed-in device 98 is formed by the cylinder insert 30 itself. Located within this second tapered feed-in device 98 is the sealing element 32 in the parking position illustrated in FIGS. 6 and 7. The sealing element 32 is provided with a radial distance to the cylinder insert 30. The radial gap resulting therefrom allows the passage of fluid and/or gas for sterilization or disinfection of the embodiment after assembly of all the components. This parking position is defined by a locking element which presently is formed by an engaging pawl 100 integrally formed onto the casing base 2. This engaging pawl 100 can be seen in particular in FIGS. 10 to 12. The engaging pawl 100 is formed by cutting free the end of the guide sleeve 76 on the drive side. The engaging pawl 100 has a locking projection 102 which is illustrated in FIGS. 9 and 10 and in the parking position engages in a locking groove 104 being formed between two ring-shaped projections 106, 108 which are integrally formed on the plunger body 4 as a single part (cf. FIG. 10). The front ring-shaped projection 108 forms an almost strictly radially extending flank of the locking groove 104, whereas the rear ring-shaped projection 106 comprises an inclined flank which facilitates the advancement of the plunger body 4 from the parking position to a pumping or operating position. In a pumping or operating position, the sealing element 32 is in sealing abutment against the inner circumferential surface of the cylinder, presently the cylinder element 30. It can be assumed that FIGS. 9 and 10 represent the uppermost pumping position and FIG. 8 the lowest pumping position. The stroke of the plunger body 4 takes place between these two positions according to FIGS. 8 and 9.

The previously described parking position is locked by the configuration of the engaging pawl 100 and the locking groove 104. Axial pressure against the plunger body 4 from the drive side beyond a critical magnitude of the pressure force leads to the parking position being released and the plunger body 4 being displaced deeper into the casing and to the pumping position. In this pumping position, the projections 106, 108 guide the plunger body 4 also relative to the guide sleeve 76 which is formed by the casing base 2 (cf. FIGS. 9, 10), as a result of which higher running smoothness of the plunger body 4 during the pumping operation is obtained. The plunger body 4 is in particular prevented from buckling when axially loaded, so that the plunger body 4 can be produced from a relatively soft material, such as, for example, plastic material.

As illustrated in FIG. 6, the plunger body 4 in the parking position projects with its hammer head 68 over the casing base 2, whereby an optical indicator for verifying the parking position is provided. After joining to the drive, when the plunger bodies 4 are necessarily transferred from the parking position to a pumping position, the ends on the drive side with the hammer head 68 are each exposed within the casing base 2 and the axially open rear recess formed there in the drive region 20.

As the description of the embodiment illustrates, the inlet and outlet passages 44, 64 are in the pump module according to the invention formed between the cylinder insert 30 and the sealing element 32. They extend within a phase boundary between the valve block 26 and the cover element 28. The inlet passage 44 provided there distributes fluid introduced from an upper end near the inlet port 18 to the respective inlet valves 41. The fluid is guided in the phase boundary up to the inlet valves 41 at the outer edge of the phase boundary and accordingly at least partially surrounds the outlet passage 64. This outlet passage 64 communicates with several outlet valves 37, two in the present case. Within the phase boundary between the cover element 28 and the valve block 26, the outlet passage 64 directs the pressurized fluid up to a collection point which is flush with the discharge passage formed by the outlet port bushing 66. The collection point is there also located within the phase boundary between the cover element 28 and the valve block 26. The largest part of the inlet passage 44 and/or the outlet passage 64 is in particular formed within the phase boundary between the valve block 26 and the cover element 28. The largest part there represents at least 50%, preferably 60%, of the total length of the flow path of the respective passage within the pump module. This flow path for the inlet side begins with the inlet opening of the inlet port 18 and ends at the inlet valve 41. The respective path on the outlet side begins with the opening formed by the outlet port bushing 66 and ends at the outlet valve 37, presently the receiving space 94 of the corresponding valve 37.

Another important aspect of the invention is the pump unit 10 which consists of the valve block 26 and the cover element 28 with the valves 37, 41 and the cylinder inserts 30 installed therein. This pump unit 10 is preassembled. The invention can there also be varied in that the cylinder is formed by the casing base 2 itself or a cylinder element which is received in the casing base 2 and which is sealingly abutted against the valve block 26. It is there conceivable that the collar, which is apparent from FIG. 7, following the first tapered feed-in device 96 abuts directly against a cylinder insert and—subject to pre-loading the casing base 2—presses the latter against the valve block 26, and in particular together with an O-ring which can be arranged at the phase boundary between the casing base 2 and the valve block 26 and thereby seals the cylinder insert thus provided.

Furthermore, it is significant that a parking position is defined in which the pump piston formed by the plunger body 4 is fixated such that the plunger body 4 is with a certain axial pressure displaced from the parking position to a pumping position. The sealing element 32 is in the parking position certainly not in abutment against the inner circumferential surface of the associated pump cylinder. The sealing element 32 is regularly provided with a radial distance from adjacent casing parts of the pump module so that the sterilization or disinfection can occur past the cylinder and the piston. All the flow-conducting parts of the pump module are there completely coated with the disinfecting or sterilizing agent and thereby effectively sterilized.

Figure 19:
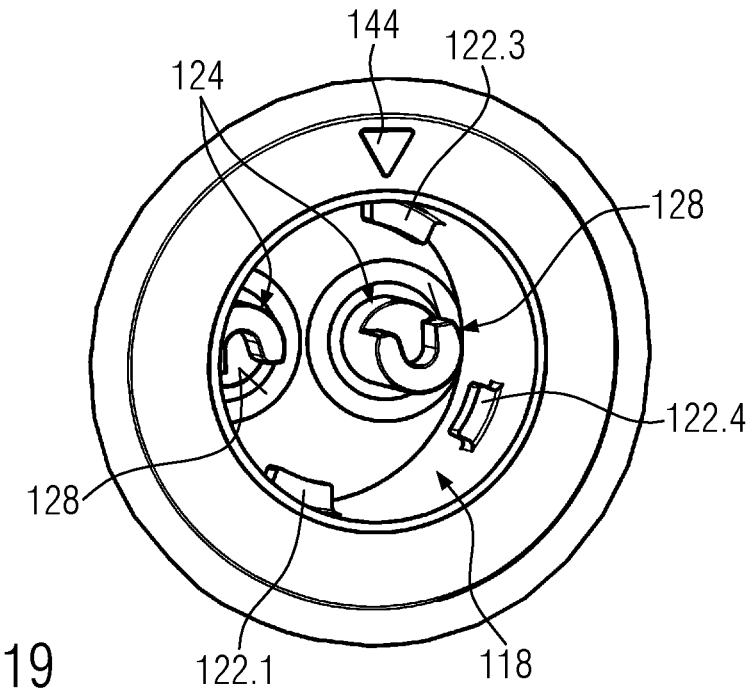
FIG. 19 shows the detail of FIG. 18 in an enlarged view without the pump module.
Figure 20:
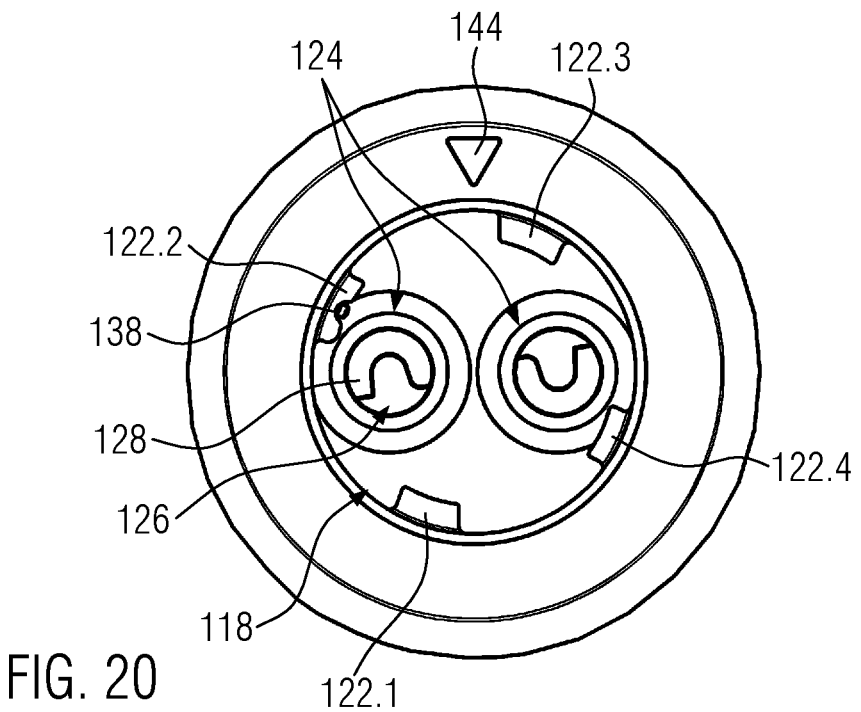
FIG. 20 shows the detail of FIG. 18 in a top view.

FIG. 19 shows a perspective side view of an embodiment of a drive unit 110 with a drive—being an electric drive—provided in a drive casing 112. A holder 114 protrudes from the drive casing 112 for holding a fluid bag. Exposed on the drive casing 112 are also various control elements 116 which serve to actuate the drive and to switch the drive on and off. Reference numeral 118 denotes a substantially cylindrical recess into which a pump module according to FIGS. 1 to 17 being denoted with reference numeral 120 is inserted and which is in comparison with these figures shown in simplified form. The casing base 2 comprises lugs 122 that protrude inwardly into the recess 118 and are embodiments of positive-locking elements of the present invention. Four lugs 122 are presently provided distributed on the circumference. The lug identified by reference numeral 122.4 has a smaller radial extension and a smaller extension in the circumferential direction than the other lugs 122.1 to 122.3 in order to allow for unique association of the pump module 120. Other types of a poka-yoke configuration are conceivable. Grooves with different angular offset relative to one another can be provided on the outer circumferential surface of the casing, in particular the casing base 2, so that the pump module 120 can be inserted into the recess 118 only in a predetermined manner. Exposed in the recess 118 are furthermore drive elements in the form of drive pushers 124 which are connected to the drive provided within drive casing 112 and which are drivable in reciprocating manner in the longitudinal direction. The drive pushers 124 form an abutment surface 126. Two drive pushers 124 are presently provided. A claw 128 being C-shaped in a top view projects over the abutment surface 126 and forms a hammer head seat 130 between itself and the abutment surface 126.

Figure 11:
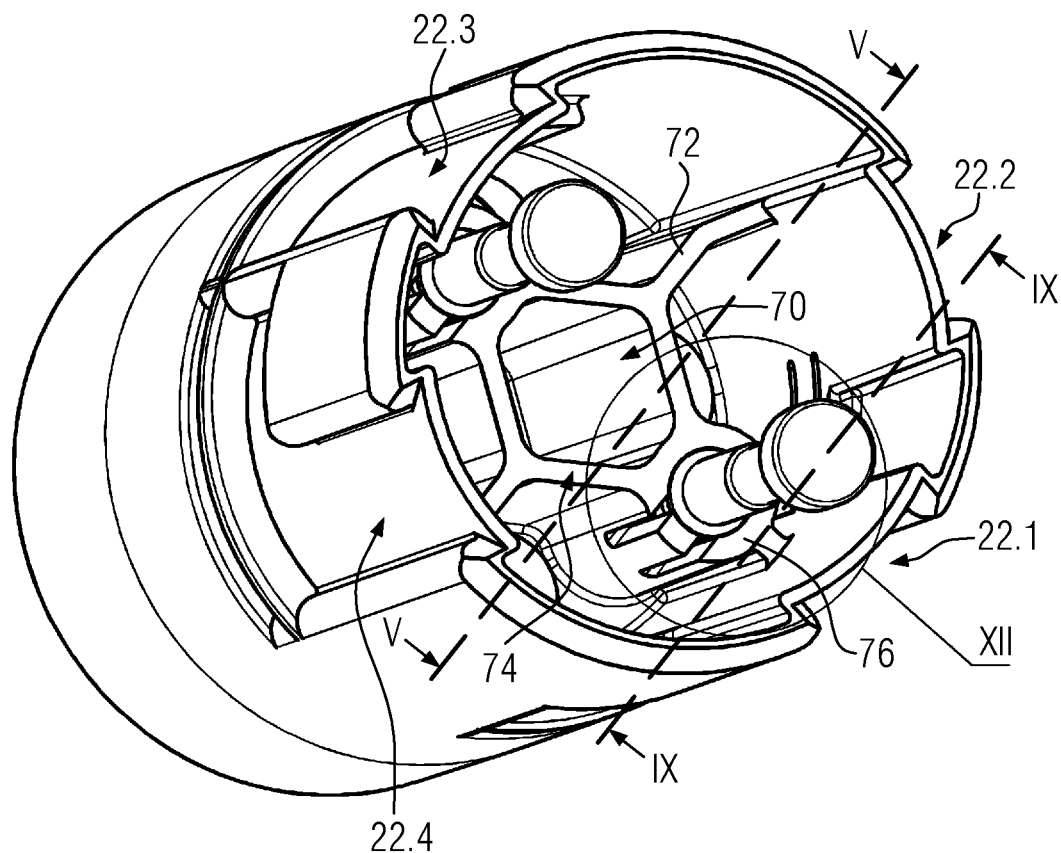
FIG. 11 shows a perspective rear view similar to FIG. 4.
Figure 12:
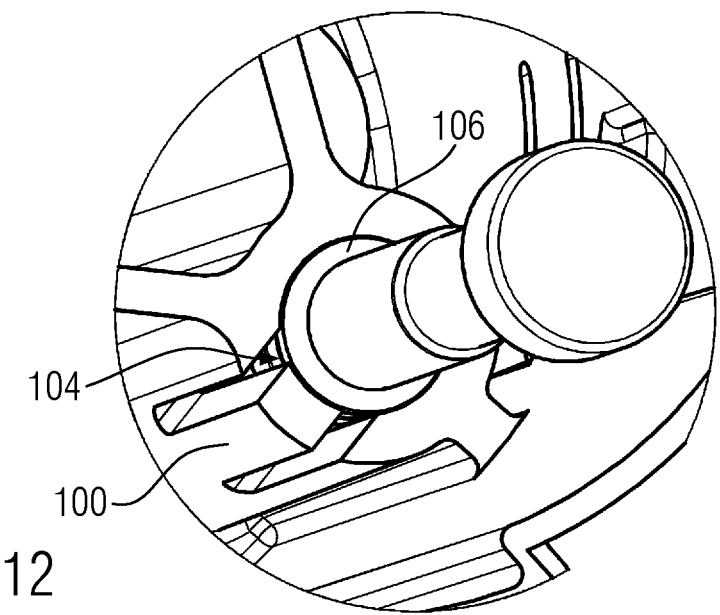
FIG. 12 shows enlarged detail XII according to FIG. 11.
Figure 16:
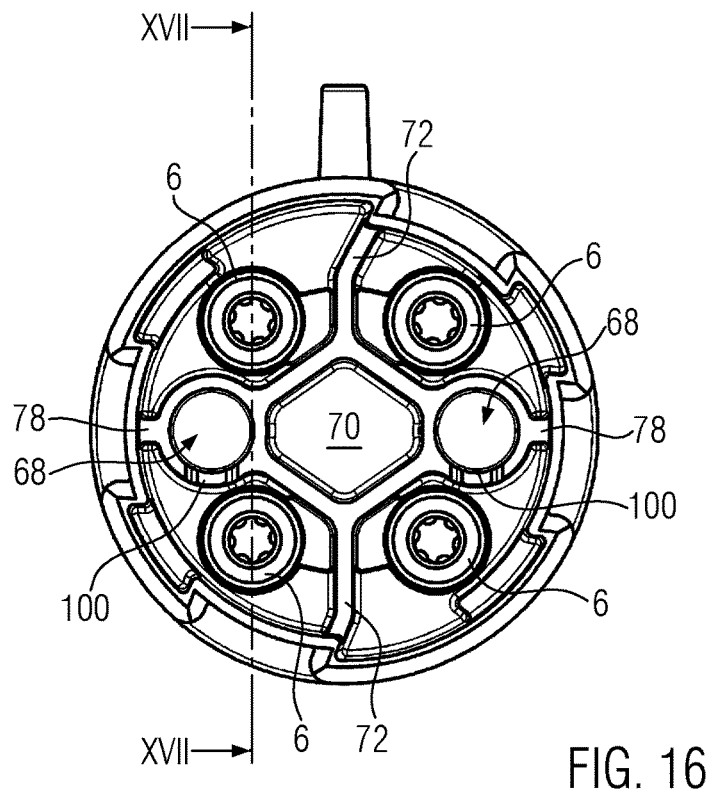
FIG. 16 shows a rear top view onto the embodiment.

As is evident in particular from FIGS. 11 and 16, of the four grooves 22 on the outer circumference of the casing base 2 extending strictly in the axial direction along the center longitudinal axis L, the groove designated with reference numeral 22.4 is formed adapted for the exact reception of the smaller lug 122.4. Due to the interaction of in particular the smaller lug 122.4 with the smaller groove 22.4, biunique orientation of the pump casing 120 is defined when joining, i.e. when inserting the pump module 120 into the recess 116. The pump module 120 can be inserted only at an angle perpendicular to a final position offset by 30° shown in FIG. 21c. This pivoted position is illustrated in FIG. 21b. The hammer head 68 projects beyond an end-side pump piston section 132 of each pump piston 4 that has a smaller diameter than the remaining pump piston 4. The hammer head 68 defines the face-side, connection-side end of the pump piston 4 and there forms a counter-surface 134 to the abutment surface 126.

The groove 22 together with the transverse groove 24 forms a guide for a bayonet lock with the respective lug 122 to first perform an axial insertion motion which then comes to an end when the lugs 122 abut against the inside lower end of the grooves 22, to thereafter be pivoted in a pivotal motion into the transverse groove 24 and thereby be axially locked. In the final position on the end side abutting against the transverse groove 24, a catch projection can be active which forms an anti-rotation lock between the pump module 112 and the drive casing 2 so that the pump module 112 is locked in its final position.

Figure 3:
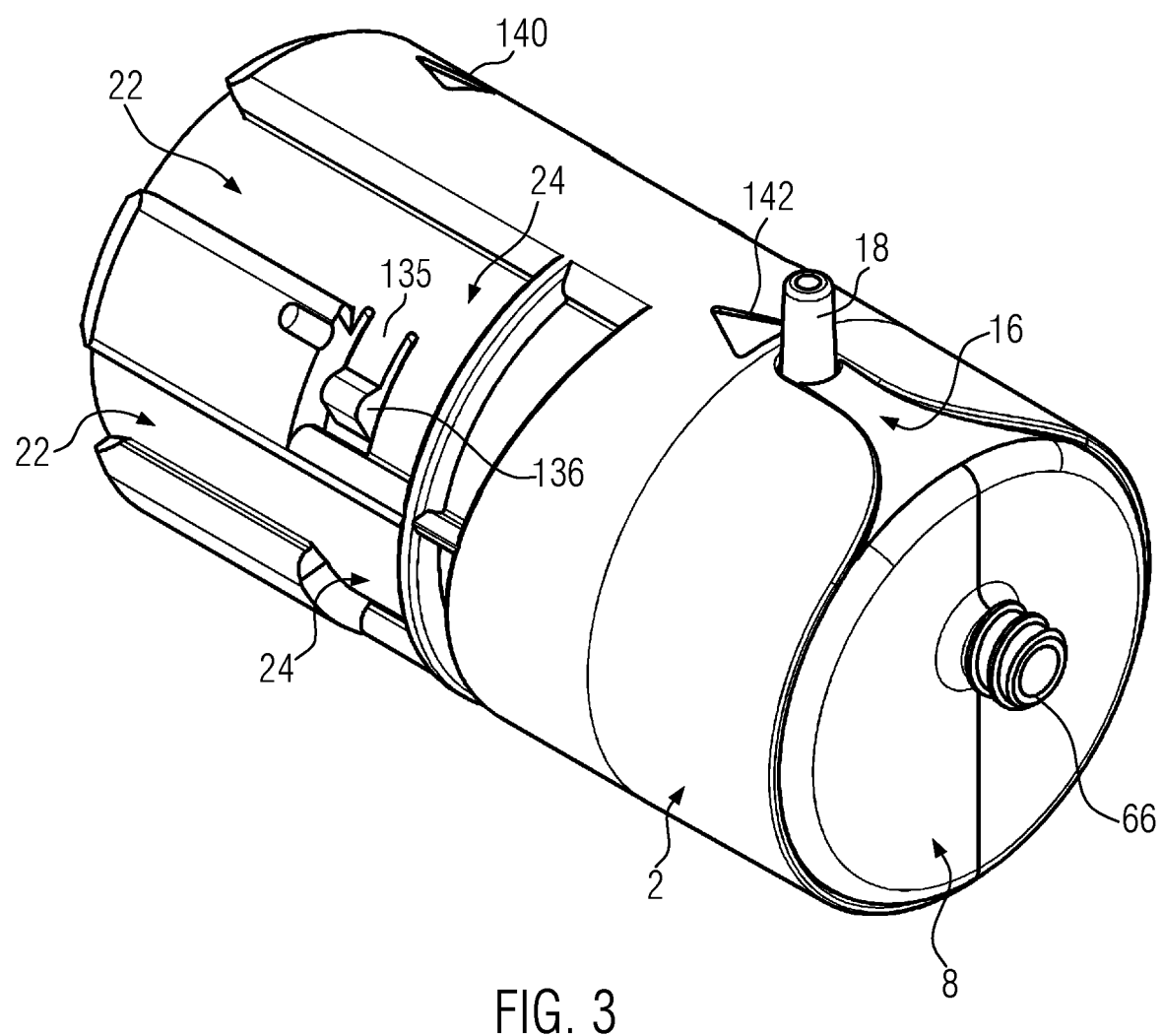
FIG. 3 shows a perspective side view according to the exploded view of FIG. 1 of the assembled pump module onto the front discharge region.
Figure 22A:
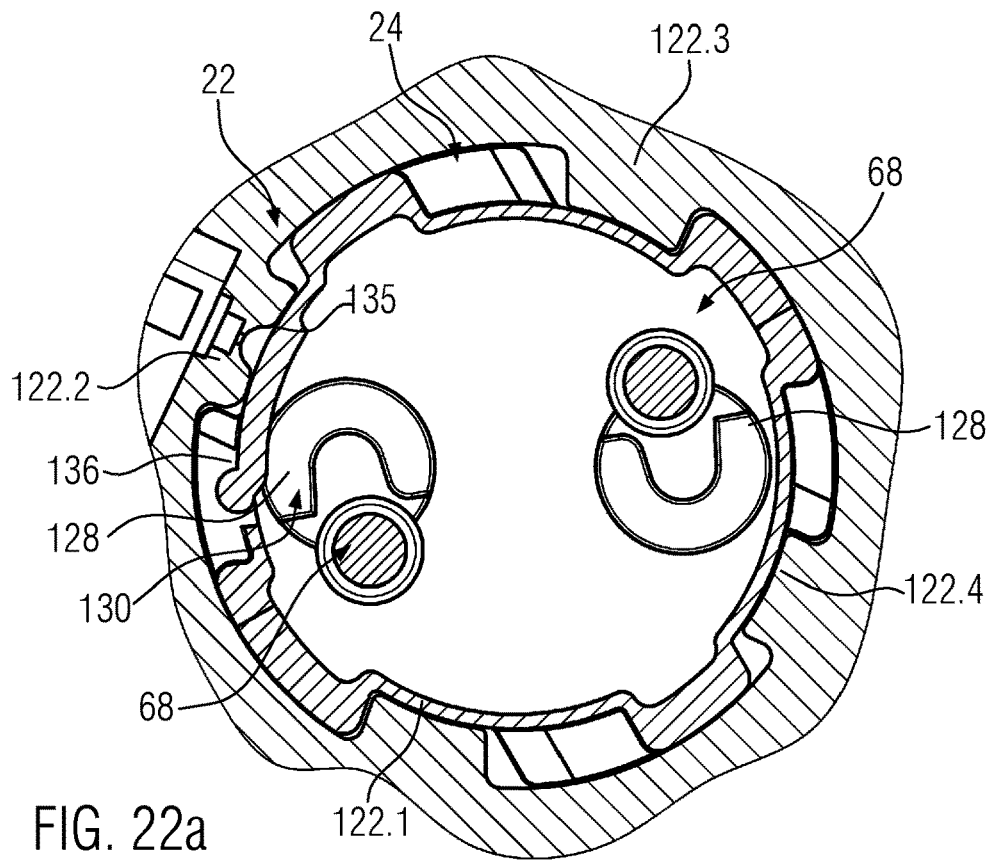

Drawn in FIG. 22a within the transverse groove 24 is further a catch and switch projection 136 formed on a spring arm and exposed in the transverse groove 24 and formed fixedly on the pump base 2 (cf. FIG. 3). This catch and switch projection 37 is associated with a switch 138 provided centrically in the lug 122.2. The switch 138 is preloaded in the radial direction inwardly relative to the recess 118 and interacts accordingly with the catch and switch projection 136. Only the actuation of this switch 138 by the catch and switch projection 136 gives rise to the possibility of driving the drive pusher 124. If the pump module 10 is accordingly not connected in the prescribed manner to the drive unit 1, then the drive unit can not be operated. The drive casing 112 is additionally provided with a reading unit which recognizes the correct orientation of the RFID ring 12 and thereby of the pump module 120 relative to the drive casing 112 and only then releases the output. This prevents operation of the device with the switch 138 being bridged.

Figure 21C:
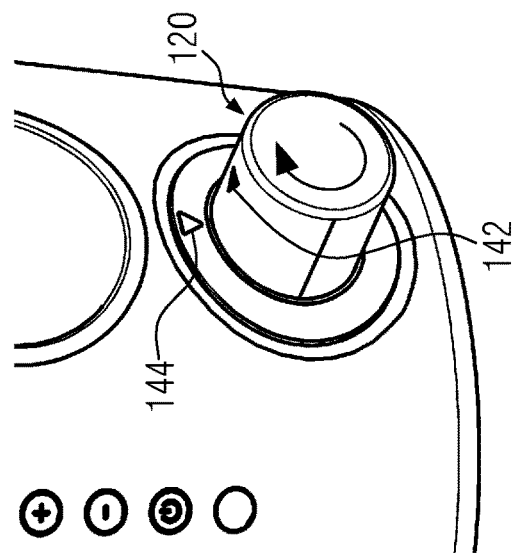
FIGS. 21a-c show a view similar to FIG. 19 with a sequence of steps for joining the pump module and FIGS. 22a-c shows partially sectional top views of the interacting ends of the drive element and the drive counter-element and their relative position when pivoting during the joining process.
Figure 21B:
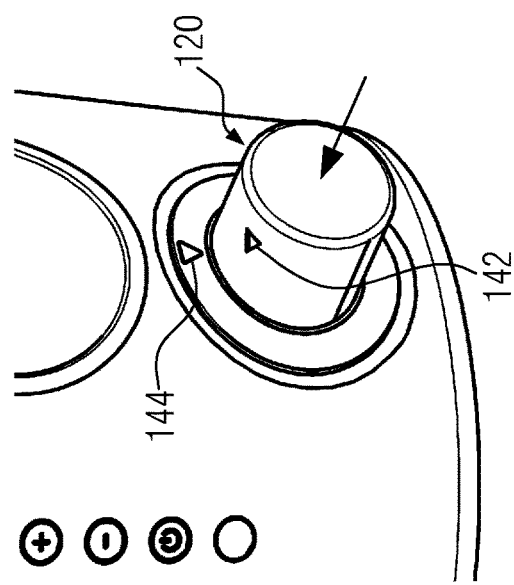
Figure 21A:
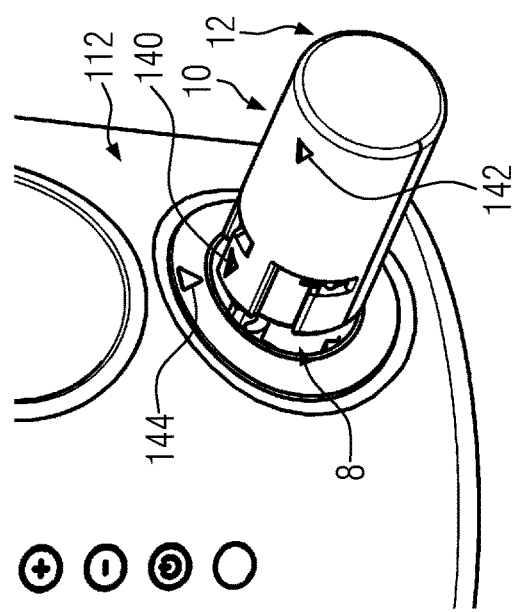

FIGS. 21a to c illustrate the insertion of the pump module 120 into the recess 118. As already mentioned above, pump module 120 is first pivoted by 30° in the counterclockwise direction relative to the final position to make the lugs 122 coincide with the grooves 22 (cf. FIG. 21a). The pivoted position is characterized by an alignment arrow 140 which can be clearly seen in FIG. 3 and is in FIG. 21a aligned with a position indicator 144 provided on the casing side. In this relative orientation, the pump module 120 can now be inserted into the recess 118. This axial insertion motion is guided by the lugs 122 which engage in the grooves 22 that are formed to correspond thereto. In the illustration according to FIG. 21b, this axial insertion, in FIG. 21b being illustrated by a straight-line arrow, is terminated. The pump module 120 is now inserted fully into the recess 118. Thereafter, the pump module 120 is pivoted by 30° in the clockwise direction, as indicated by the arrow in FIG. 21c. Following this pivotal motion by 30°, the pump module 120 has reached its final position. The final position is indicated to the user by a directional arrow 142 which is provided on the outer periphery of the casing base 2 and which is in the final position aligned with a position indicator 144 provided on the drive casing 2. The directional arrow 142 also indicates the direction of insertion for the pump module 2 into the recess 8.

When joining the pump module 120 and the drive casing 112, the drive pushers 124 and the pump pistons 4 are approximate to each other. Due to the axial guidance of the lugs 122 in the grooves 22, the counter-surface 134 formed by the hammer head 68 is at least in part located above the abutment surface 126 formed by the drive pusher 124 (cf. FIG. 22a). A progressive axial motion finally leads to the pump piston 4 being in abutment at the end side against the abutment surface 126. As the pump module 120 continues to approach the drive casing 112, the parking position is released and the pump piston 4 is forced deeper into the casing base 2 and to a pumping position. No further relative axial motion between the drive pusher 124 and the associated pump piston 4 is thereafter given.

The respective hammer head 68 of the two pump pistons 4 is there located in an eccentric position relative to the center of the drive pusher 124, which is shown in FIG. 22a. The casing base 2 is after the axial abutment of both pump pistons 30 against the drive pushers 124 typically displaced by a further minor distance axially relative to the drive casing 2, so that it is ensured that axial abutment of the pump piston 4 is always reliably obtained against the drive pusher 124 until the axial final position has been reached when joining the pump module 120 and drive casing 112, before casing base 2 is pivoted relative to the drive casing 112. The configuration is certainly to be such that reliable abutment of the pump piston 4 against the drive pusher 124 is after completion of the axial insertion motion obtained in any conceivable position of drive pusher 124, even in a position where the drive pusher 124 is in the lowest position within the recess 8.

Figure 22B:
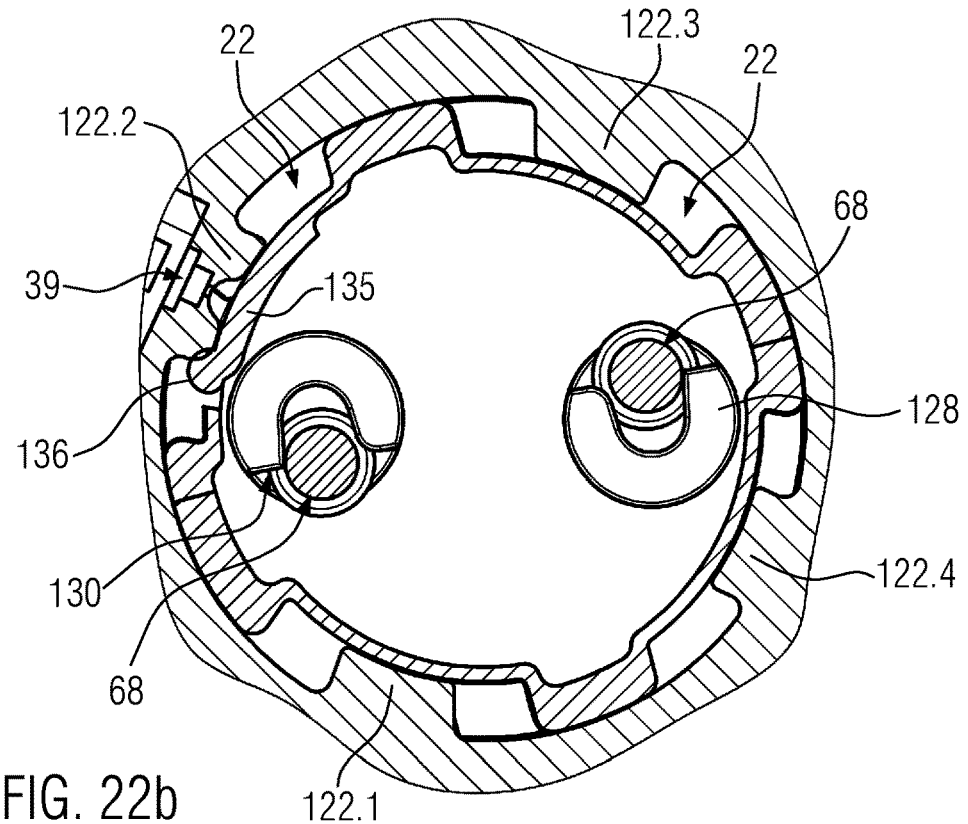
Figure 22C:
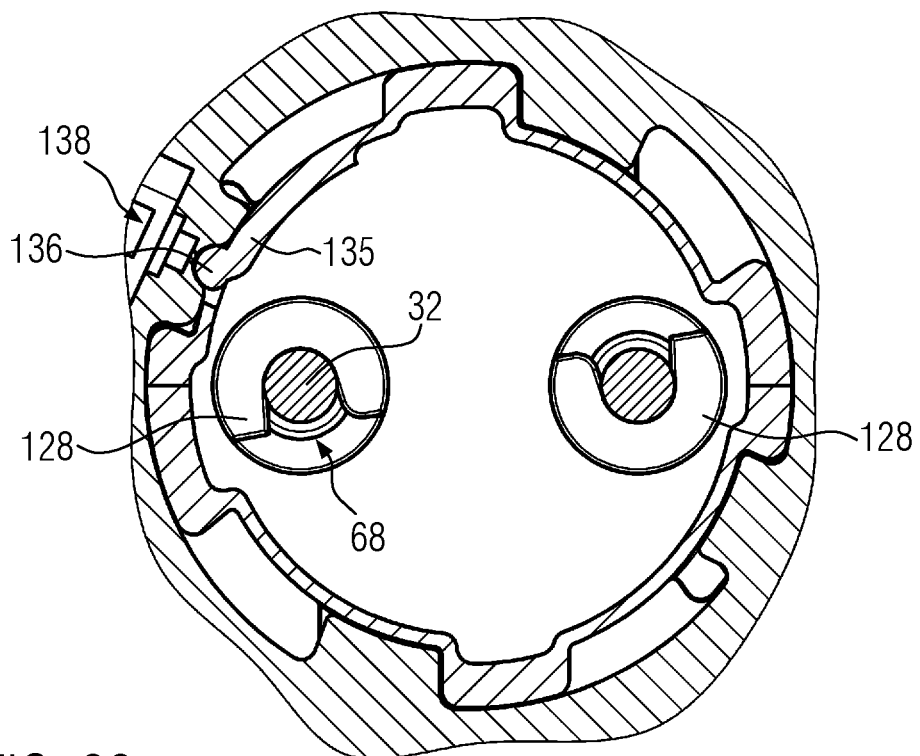

After this axial final position has been reached, the pump module 120 is then pivoted in the clockwise direction. The hammer heads 68 being disposed eccentric to the center of this pivotal motion are thereby—as illustrated in FIGS. 22a to 22c—with their counter-surface 134 in a sliding manner displaced on the abutment surface 126 relative to drive pusher 124, namely in a plane extending perpendicular to the direction of insertion. The previously eccentric arrangement of the pump pistons 4 relative to drive pushers 124 according to FIG. 22a therafter, via an intermediate position shown in FIG. 22b, approaches the final position shown in FIG. 22c. In this final position, the lugs 122 abut against stops which are formed by the transverse grooves 24. The casing base 2 is commonly locked against the drive casing 2. The pump pistons 4 are arranged substantially concentric to the drive pushers 124. Each claw 128 engages over the associated hammer head 68. The hammer head 68 is by engagement of the hammer head seat 130 comprising the claw 128 held in an axially positive-locking manner. The hammer head seat 130 is typically in the axial direction matched exactly to the height of the hammer head 68 so that a play-free axial positive-locking connection between drive pusher 124 and the pump piston 4 arises.

LIST OF REFERENCE NUMERALS 2 casing base
4 plunger body/pump piston
6 tensioning screw:
8 head element
10 pump unit
12 RFID ring
14 discharge region
16 axial slot
18 inlet port
20 drive region
22 groove
24 transverse groove
26 valve block
28 cover element
30 cylinder insert
32 sealing element
34 valve liner
36 valve ball
37 outlet valve
38 valve liner
40 valve ball
41 inlet valve
42 inlet valve bore
44 inlet passage
46 projection
50 outlet valve bore
52 fitting element
54 sealing surface
56 fitting bore
58 outlet bore
60 through bores
62 annular surface
64 outlet passage
66 outlet port bushing
68 hammer head
70 center recess
72 radial web
74 polygon structure
76 guide sleeve
78 further radial web
80 partition wall
82 passage bore
83 sealing ring
84 cylinder insert receiving bore
86 ring collar
88 support rib
90 sleeve segment
92 passage bore
94 receiving space
96 first tapered feed-in device
98 second tapered feed-in device
100 engaging pawl
102 locking projection
104 locking groove
106 ring-shaped projection
108 ring-shaped projection
110 drive unit
112 drive casing
114 holder
116 control element
118 recess
120 pump module
122 lugs
124 drive pusher
126 abutment surface 128 claw
130 hammer head seat
132 pump piston section
134 counter-surface
135 spring arm
136 catch and switch projection
138 switch
140 alignment arrow
142 directional arrow
144 position indicator
L center longitudinal axis

The invention claimed is:

1. A pump module comprising: a pump casing, a cylinder, at least one pump piston, which is mounted in a reciprocatingly movable manner in the pump casing and which is provided with at least one sealing element that interacts with the cylinder during a pumping operation; said pump casing comprising:
  a valve block which is sealed against the cylinder and receives at least one valve to said cylinder, and
  a cover element on a side opposite to said cylinder being in abutment against said valve block, wherein said cover element is fixed to said valve block forming an inlet passage to said cylinder and an outlet passage communicating with said cylinder each formed by a recessed groove which is exposed toward a surface of the cover element, wherein the grooves are each formed by the valve block on a side facing away from the cylinder of the valve block, wherein the grooves by an interaction of the valve block and the cover element become circumferentially closed, and wherein the inlet passage and the outlet passage each extend perpendicular to a reciprocating direction of the pump piston.

2. The pump module according to claim 1, wherein said valve block comprises a port for fluid to be conveyed in said pump module.

3. The pump module according to claim 1, wherein said cylinder abuts against said valve block in a sealing manner.

4. The pump module according to claim 3, wherein said cylinder is fastened to said valve block.

5. The pump module according to claim 3, wherein said cylinder at an end side abuts against a valve liner provided in said valve block.

6. The pump module according to claim 1, including a pre-assembled pump unit comprising said cylinder, said valve block, and said cover element.

7. The pump module according to claim 1, wherein the pump casing forms a discharge region for receiving said valve block and a drive region for receiving said cylinder and said pump piston.

8. The pump module according to claim 1, wherein said inlet passage is provided in a phase boundary between said cover element and said valve block is in communication with at least two cylinders, and that said inlet passage is formed within the phase boundary such that said inlet passage at least partially circumferentially surrounds said outlet passage.

9. The pump module according to claim 1, wherein the pump casing comprises a casing base forming a guide sleeve upstream of said cylinder, the guide sleeve guiding the pump piston.

10. The pump module according to claim 9, wherein the casing base forms guide and locking surfaces for detachably fastening said pump module to a drive casing of a drive, said drive having a drive pusher which is connectable to said pump piston for reciprocating operation of said pump piston.

11. The pump module according to claim 1, wherein a head element, which is provided upstream of said cover element, is provided with an outlet port and is in tight abutment against said cover element.

12. The pump module according to claim 1, including a transponder element attached to said pump casing.

13. The pump module of claim 1, wherein the cover element has a bore defining an outlet for a fluid conveyed, wherein the cover element tightly abuts against a head element for providing a seal between the outlet and a stud-shaped outlet port located on one face of said pump module.

14. The pump module according to claim 9, wherein said casing base, said valve block, and said cover element are formed as plastic parts.

* * * * *